(12) United States Patent
Degnan

(10) Patent No.: US 9,695,176 B2
(45) Date of Patent: Jul. 4, 2017

(54) SUBSTITUTED IMIDAZO[1,5-A]PYRAZINES AS CGRP RECEPTOR ANTAGONISTS

(71) Applicant: BRISTOL-MYERS SQUIBB COMPANY, Princeton, NJ (US)

(72) Inventor: Andrew P. Degnan, Rocky Hill, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 142 days.

(21) Appl. No.: 14/433,693

(22) PCT Filed: Oct. 14, 2013

(86) PCT No.: PCT/US2013/064791
§ 371 (c)(1),
(2) Date: Apr. 6, 2015

(87) PCT Pub. No.: WO2014/062548
PCT Pub. Date: Apr. 24, 2014

(65) Prior Publication Data
US 2015/0274734 A1 Oct. 1, 2015

Related U.S. Application Data

(60) Provisional application No. 61/715,446, filed on Oct. 18, 2012.

(51) Int. Cl.
*A61K 31/4985* (2006.01)
*C07D 487/04* (2006.01)

(52) U.S. Cl.
CPC .................. *C07D 487/04* (2013.01)

(58) Field of Classification Search
CPC .......................... A61K 31/4985; C07D 487/04
USPC .......................................... 514/249; 544/350
See application file for complete search history.

(56) References Cited

U.S. PATENT DOCUMENTS

| 6,843,269 B2 | 1/2005 | Verma et al. |
| 7,220,862 B2 | 5/2007 | Chaturvedula et al. |
| 7,314,883 B2 | 1/2008 | Chen et al. |
| 7,569,578 B2 | 8/2009 | Luo et al. |
| 7,754,732 B2 | 7/2010 | Chaturvedula et al. |
| 7,842,808 B2 | 11/2010 | Chaturvedula et al. |

FOREIGN PATENT DOCUMENTS

WO  WO 2014/062548  *  4/2014

OTHER PUBLICATIONS

Jordan, V. C. Nature Reviews: Drug Discovery, 2, 2003, 205.*
Hackam, et al. JAMA, 296(14), 2006, 1731-1732.*
Tora, G. et al., "Preparation of imidazoles as potent calcitonin gene-related peptide (CGRP) antagonists", Bioorganic & Medicinal Chemistry Letters, vol. 23, pp. 5684-5688 (2013).

* cited by examiner

*Primary Examiner* — Douglas M Willis
(74) *Attorney, Agent, or Firm* — James Epperson

(57) ABSTRACT

The disclosure generally relates to the novel compounds of formula I, including pharmaceutically acceptable salts, which are CGRP receptor antagonists. The disclosure also relates to pharmaceutical compositions and methods for using the compounds in the treatment of CGRP related disorders including migraine and other headaches, neurogenic vasodilation, neurogenic inflammation, thermal injury, circulatory shock, flushing associated with menopause, airway inflammatory diseases such as asthma, and chronic obstructive pulmonary disease (COPD).

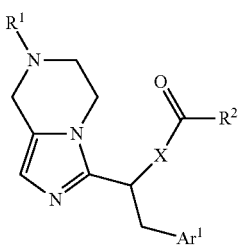

9 Claims, No Drawings

SUBSTITUTED IMIDAZO[1,5-A]PYRAZINES AS CGRP RECEPTOR ANTAGONISTS

BACKGROUND OF THE INVENTION

The disclosure generally relates to the novel compounds of formula I, including pharmaceutically acceptable salts, which are CGRP-receptor antagonists. The disclosure also relates to pharmaceutical compositions and methods for using the compounds in the treatment of CGRP related disorders including migraine headaches, neurogenic vasodilation, neurogenic inflammation, thermal injury, circulatory shock, flushing associated with menopause, airway inflammatory diseases such as asthma, and chronic obstructive pulmonary disease (COPD).

Calcitonin gene-related peptide (CGRP) is a naturally occurring 37-amino-acid peptide first identified in 1982 (Amara, S. G. et al, Science 1982, 298, 240-244). Two forms of the peptide are expressed (αCGRP and βCGRP) which differ by one and three amino acids in rats and humans, respectively. The peptide is widely distributed in both the peripheral (PNS) and central nervous system (CNS), principally localized in sensory afferent and central neurons, and displays a number of biological effects, including vasodilation.

When released from the cell, CGRP binds to specific cell surface G protein-coupled receptors and exerts its biological action predominantly by activation of intracellular adenylate cyclase (Poyner, D. R. et al, Br J Pharmacol 1992, 105, 441-7; Van Valen, F. et al, Neurosci Lett 1990, 119, 195-8.). Two classes of CGRP receptors, CGRP1 and CGRP2, have been proposed based on the antagonist properties of the peptide fragment CGRP(8-37) and the ability of linear analogues of CGRP to activate CGRP2 receptors (Juaneda, C. et al. TiPS 2000, 21, 432-438). However, there is lack of molecular evidence for the CGRP2 receptor (Brain, S. D. et al, TiPS 2002, 23, 51-53). The CGRP1 receptor has three components: (i) a 7 transmembrane calcitonin receptor-like receptor (CRLR); (ii) the single transmembrane receptor activity modifying protein type one (RAMP1); and (iii) the intracellular receptor component protein (RCP) (Evans B. N. et al., J Biol Chem. 2000, 275, 31438-43). RAMP1 is required for transport of CRLR to the plasma membrane and for ligand binding to the CGRP-receptor (McLatchie, L. M. et al, Nature 1998, 393, 333-339). RCP is required for signal transduction (Evans B. N. et al., J Biol Chem. 2000, 275, 31438-43). There are known species—specific differences in binding of small molecule antagonists to the CGRP—receptor with typically greater affinity seen for antagonism of the human receptor than for other species (Brain, S. D. et al, TiPS 2002, 23, 51-53). The amino acid sequence of RAMP1 determines the species selectivity, in particular, the amino acid residue Trp74 is responsible for the phenotype of the human receptor (Mallee et al. J Biol Chem 2002, 277, 14294-8).

Inhibitors at the receptor level to CGRP are postulated to be useful in pathophysiologic conditions where excessive CGRP receptor activation has occurred. Some of these include neurogenic vasodilation, neurogenic inflammation, migraine, cluster headache and other headaches, thermal injury, circulatory shock, menopausal flushing, and asthma. CGRP receptor activation has been implicated in the pathogenesis of migraine headache (Edvinsson L. CNS Drugs 2001; 15(10):745-53; Williamson, D. J. Microsc. Res. Tech. 2001, 53, 167-178.; Grant, A. D. Brit. J. Pharmacol. 2002, 135, 356-362.). Serum levels of CGRP are elevated during migraine (Goadsby P J, et al. Ann Neurol 1990; 28:183-7) and treatment with anti-migraine drugs returns CGRP levels to normal coincident with alleviation of headache (Gallai V. et al. Cephalalgia 1995; 15: 384-90). Migraineurs exhibit elevated basal CGRP levels compared to controls (Ashina M, et al., Pain 2000, 86(1-2):133-8.2000). Intravenous CGRP infusion produces lasting headache in migraineurs (Lassen L H, et al. Cephalalgia 2002 February; 22(1):54-61). Preclinical studies in dog and rat report that systemic CGRP blockade with the peptide antagonist CGRP(8-37) does not alter resting systemic hemodynamics nor regional blood flow (Shen, Y-T. et al, J Pharmacol Exp Ther 2001, 298, 551-8). Thus, CGRP-receptor antagonists may present a novel treatment for migraine that avoids the cardiovascular liabilities of active vasoconstriction associated with non-selective 5-HT1B/1D agonists, 'triptans' (e.g., sumatriptan).

CGRP antagonists have shown efficacy in human clinical trials. See Davis C D, Xu C. Curr Top Med Chem. 2008 8(16):1468-79; Benemei S, Nicoletti P, Capone J G, Geppetti P. Curr Opin Pharmacol. 2009 9(1):9-14. Epub 2009 Jan. 20; Ho T W, Ferrari M D, Dodick D W, Galet V, Kost J, Fan X, Leibensperger H, Froman S, Assaid C, Lines C, Koppen H, Winner P K. Lancet. 2008 372:2115. Epub 2008 Nov. 25; Ho T W, Mannix L K, Fan X, Assaid C, Furtek C, Jones C J, Lines C R, Rapoport A M; Neurology 2008 70:1304. Epub 2007 Oct. 3.

CGRP receptor antagonists have been disclosed. See U.S. Pat. No. 7,569,578 and US patent application publication 20100324023.

DESCRIPTION OF THE INVENTION

The invention encompasses a series of CGRP antagonist compounds including pharmaceutically acceptable salts, compositions, methods of making them, and methods of using them in therapeutic treatment.

One aspect of the invention is a compound of formula I

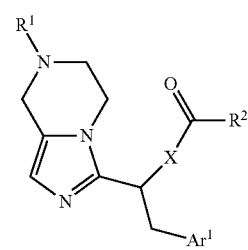

where:

$R^1$ is hydrogen, alkyl, cycloalkyl, or $(Ar^2)$alkyl;

$R^2$ is piperidinyl substituted with 1 substituent selected from the group consisting of

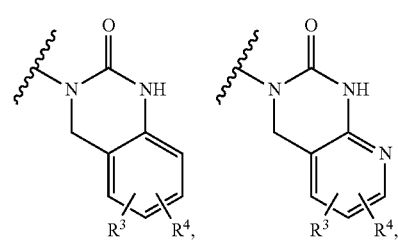

-continued

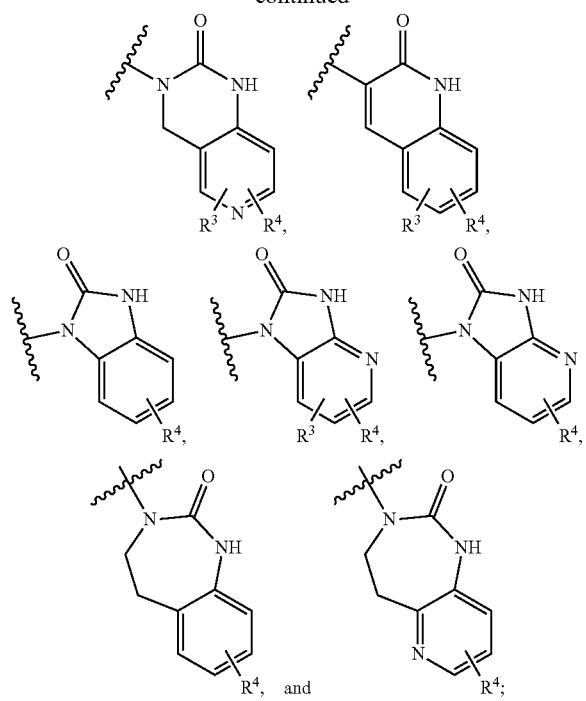

R³ is hydrogen, halo, cyano, alkyl, haloalkyl, alkoxy, or haloalkoxy;

R⁴ is hydrogen, halo, cyano, alkyl, haloalkyl, alkoxy, or haloalkoxy;

Ar¹ is indazolyl substituted with 0-1 substituents selected from the group consisting of halo, alkyl, and haloalkyl;

Ar² is phenyl substituted with 0-3 substituents selected from the group consisting of halo, alkyl, haloalkyl, alkoxy, and haloalkoxy; and X is O, CH₂, or NH;

or a pharmaceutically acceptable salt thereof.

Another aspect of the invention is a compound of formula I where R¹ is hydrogen, alkyl, cycloalkyl, or (Ar²)alkyl; R² is piperidinyl substituted with 1 substituent selected from the group consisting of

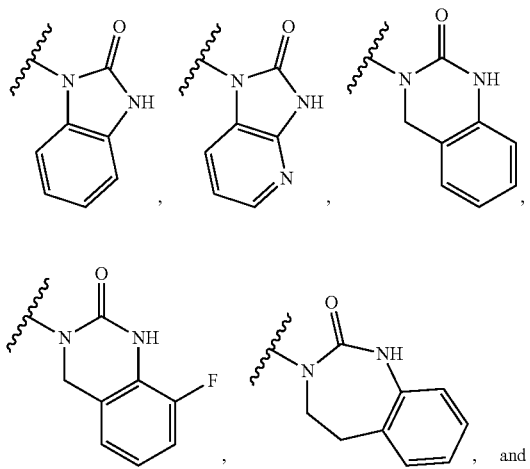

-continued

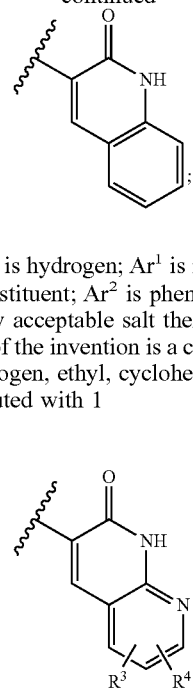

R³ is hydrogen; R⁴ is hydrogen; Ar¹ is indazolyl substituted with 1 alkyl substituent; Ar² is phenyl; and X is O; or a pharmaceutically acceptable salt thereof.

Another aspect of the invention is a compound of formula I where R¹ is hydrogen, ethyl, cyclohexyl, or benzyl; R² is piperidinyl substituted with 1

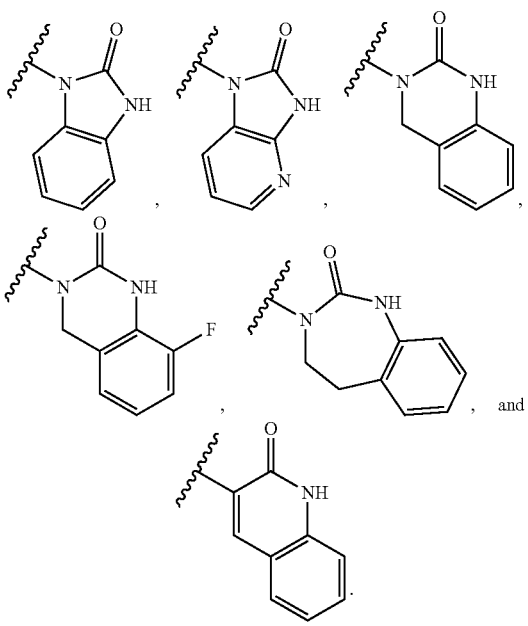

substituent; R³ is hydrogen; R⁴ is hydrogen; Ar¹ is indazolyl substituted with 1 methyl substituent; Ar² is phenyl; and X is O; or a pharmaceutically acceptable salt thereof.

Another aspect of the invention is a compound of formula I where R¹ is hydrogen, ethyl, cyclohexyl, or benzyl.

Another aspect of the invention is a compound of formula I where R² is piperidinyl 4-substituted with 1 substituent selected from the group consisting of Another aspect of the invention is a compound of formula I where Ar¹ is indazolyl substituted with 1 alkyl substituent.

Another aspect of the invention is a compound of formula I where Ar² is phenyl.

Another aspect of the invention is a compound of formula I where X is O.

Another aspect of the invention is a compound of formula I with the designated stereochemistry.

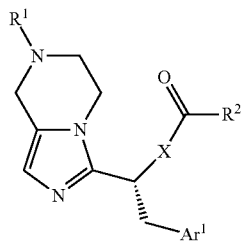

The scope of any instance of a variable, including $R^1$, $R^2$, $R^3$, $R^4$, $Ar^1$, $Ar^2$, and X, can be used independently with the scope of any other instance of a variable substituent. As such, the invention includes combinations of the different aspects.

Unless specified otherwise, these terms have the following meanings "Halo" includes fluoro, chloro, bromo, and iodo. "Haloalkyl" and "haloalkoxy" include all halogenated isomers from monohalo to perhalo. "Alkyl" means a straight or branched alkyl group composed of 1 to 6 carbons. "Alkenyl" means a straight or branched alkyl group composed of 2 to 6 carbons with at least one double bond. "Alkynyl" means a straight or branched alkyl group composed of 2 to 6 carbons with at least one triple bond. "Cycloalkyl" means a monocyclic ring system composed of 3 to 7 carbons. Terms with a hydrocarbon moiety (e.g. alkoxy) include straight and branched isomers for the hydrocarbon portion. "Aryl" means a monocyclic or bicyclic aromatic hydrocarbon groups having 6 to 12 carbon atoms, or a bicyclic fused ring system wherein one or both of the rings is a phenyl group. Bicyclic fused ring systems consist of a phenyl group fused to a four- to six-membered aromatic or non-aromatic carbocyclic ring. Representative examples of aryl groups include, but are not limited to, indanyl, indenyl, naphthyl, phenyl, and tetrahydronaphthyl. "Heteroaryl" means a 5 to 7 membered monocyclic or 8 to 11 membered bicyclic aromatic ring system with 1-5 heteroatoms independently selected from nitrogen, oxygen, and sulfur. Parenthetic and multiparenthetic terms are intended to clarify bonding relationships to those skilled in the art. For example, a term such as ((R)alkyl) means an alkyl substituent further substituted with the substituent R.

The invention includes all pharmaceutically acceptable salt forms of the compounds. Pharmaceutically acceptable salts are those in which the counter ions do not contribute significantly to the physiological activity or toxicity of the compounds and as such function as pharmacological equivalents. These salts can be made according to common organic techniques employing commercially available reagents. Some anionic salt forms include acetate, acistrate, besylate, bromide, chloride, citrate, fumarate, glucouronate, hydrobromide, hydrochloride, hydroiodide, iodide, lactate, maleate, mesylate, nitrate, pamoate, phosphate, succinate, sulfate, tartrate, tosylate, and xinofoate. Some cationic salt forms include ammonium, aluminum, benzathine, bismuth, calcium, choline, diethylamine, diethanolamine, lithium, magnesium, meglumine, 4-phenylcyclohexylamine, piperazine, potassium, sodium, tromethamine, and zinc.

Some compounds of the invention may exist in stereoisomeric forms, one example of which is shown below. The invention includes all stereoisomeric and tautomeric forms of the compounds.

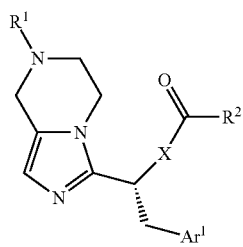

The invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds may have a variety of potential uses, for example as standards and reagents in determining biological activity. In the case of stable isotopes, such compounds may have the potential to favorably modify biological, pharmacological, or pharmacokinetic properties.

Synthetic Methods

The compounds may be made by methods known in the art including those described below and including variations within the skill of the art. Some reagents and intermediates are known in the art. Other reagents and intermediates can be made by methods known in the art using readily available materials. The following methods are for illustrative purposes and are not intended to limit the scope of the invention. It will be appreciated by those skilled in the art that there are a number of methods available for the synthesis of these compounds and that their synthesis is not limited to the methods provided in the following examples. Variations of the compounds and the procedures to make them which are not illustrated are within the skill of the art. The variables describing general structural formulas and features in the synthetic schemes are distinct from and should not be confused with the variables in the claims or the rest of the specification. These variables are meant only to illustrate how to make some of the compounds of the invention.

Some Formula I compounds can be synthesized through the following general schemes.

Scheme 1.

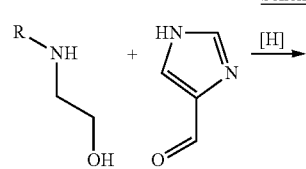

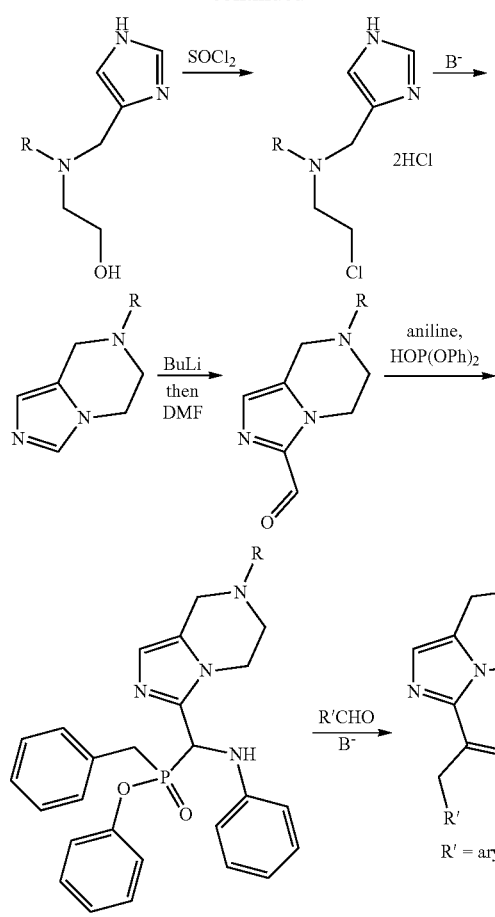
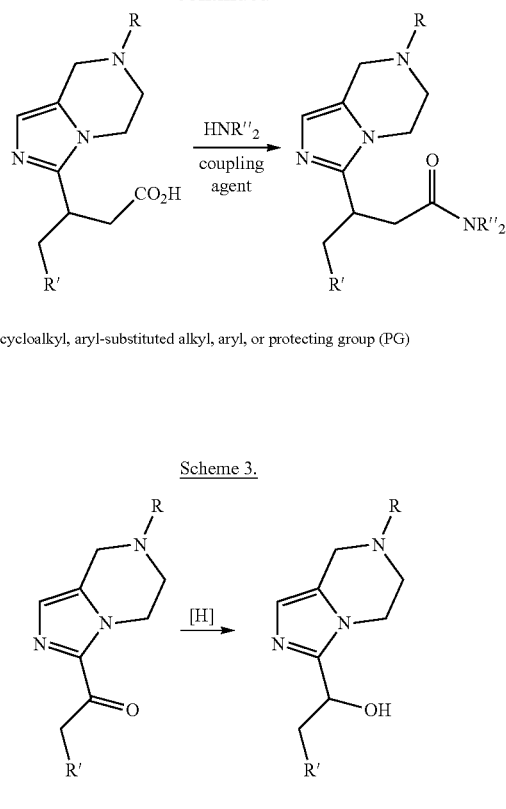
R' = aryl
R = alkyl, cycloalkyl, aryl-substituted alkyl, aryl, or protecting group (PG)
Scheme 2.
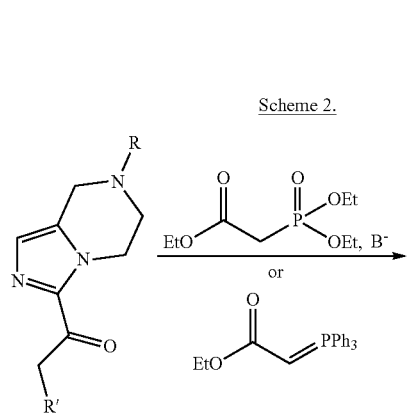
Scheme 3.
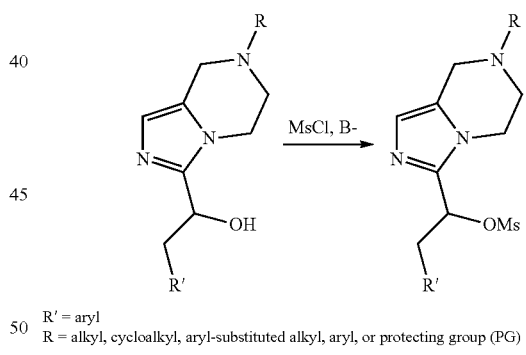
R' = aryl
R = alkyl, cycloalkyl, aryl-substituted alkyl, aryl, or protecting group (PG)
Scheme 4.
Scheme 5.
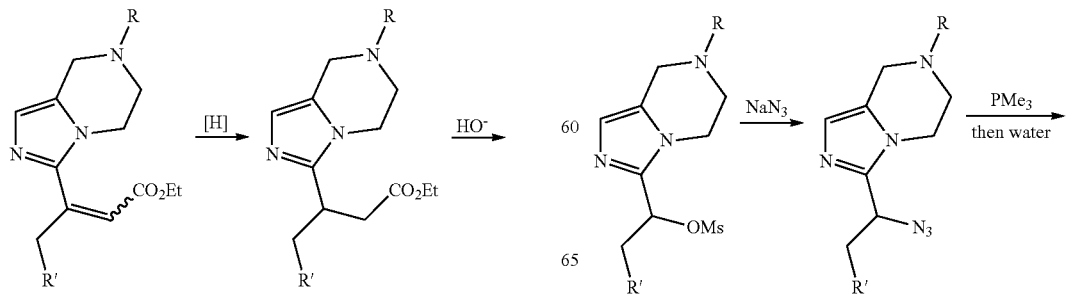
R' = aryl
R = alkyl, cycloalkyl, aryl-substituted alkyl, aryl, or protecting group (PG)

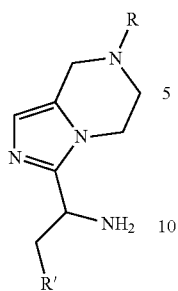
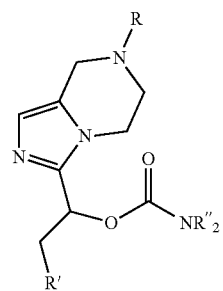
R' = aryl
R = alkyl, cycloalkyl, aryl-substituted alkyl, aryl, or protecting group (PG)
R' = aryl
R = alkyl, cycloalkyl, aryl-substituted alkyl, aryl, or protecting group (PG)
Scheme 6.
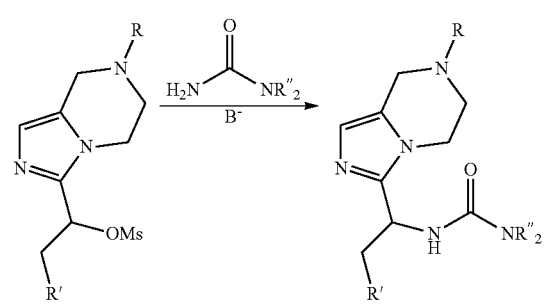
Scheme 9.
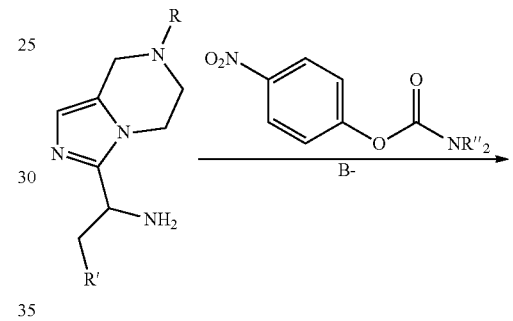
R' = aryl
R = alkyl, cycloalkyl, aryl-substituted alkyl, aryl, or protecting group (PG)
Scheme 7.
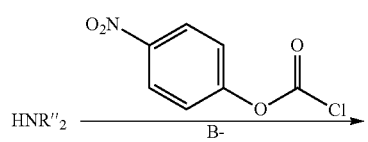
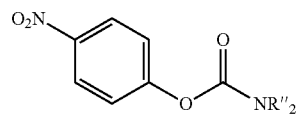
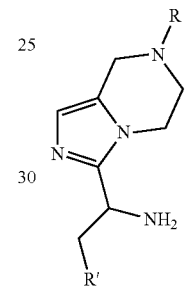
R' = aryl
R = alkyl, cycloalkyl, aryl-substituted alkyl, aryl, or protecting group (PG)
Scheme 8.
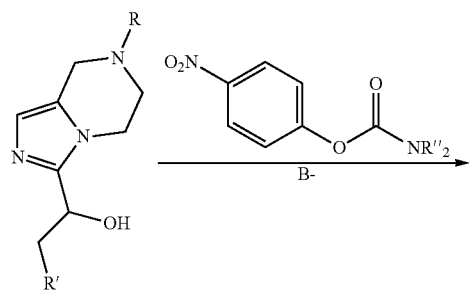
Scheme 10.
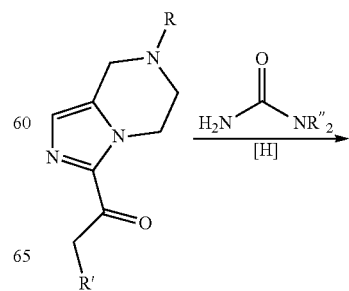

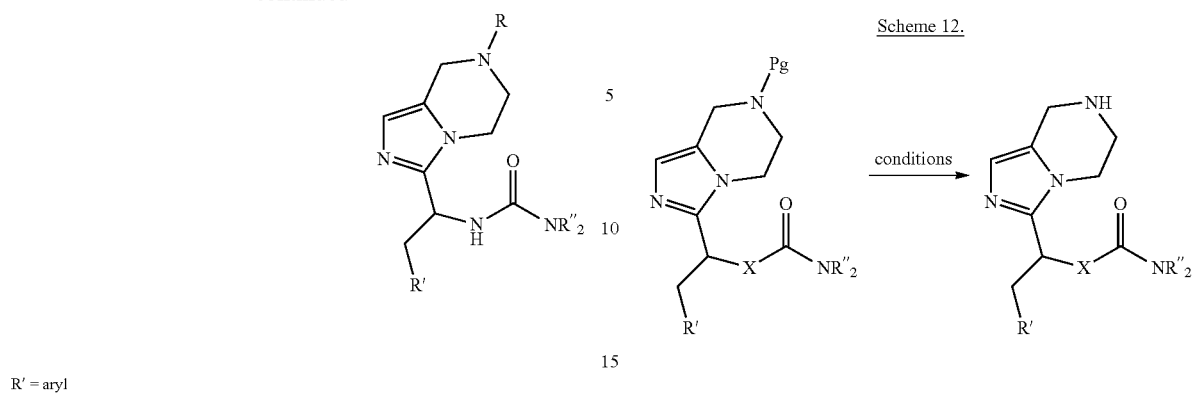

R' = aryl
R = alkyl, cycloalkyl, aryl-substituted alkyl, aryl, or protecting group (PG)

Scheme 12.

R' = aryl
PG = protecting group
X = O, NH, CH₂

Scheme 11.

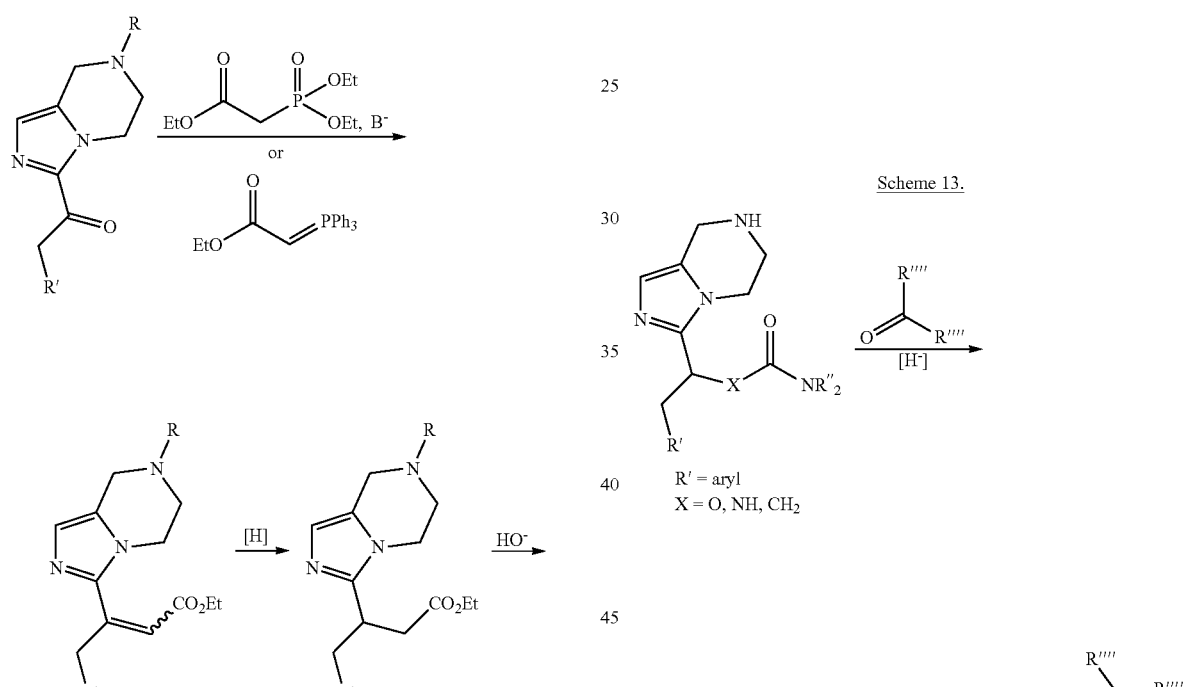

Scheme 13.

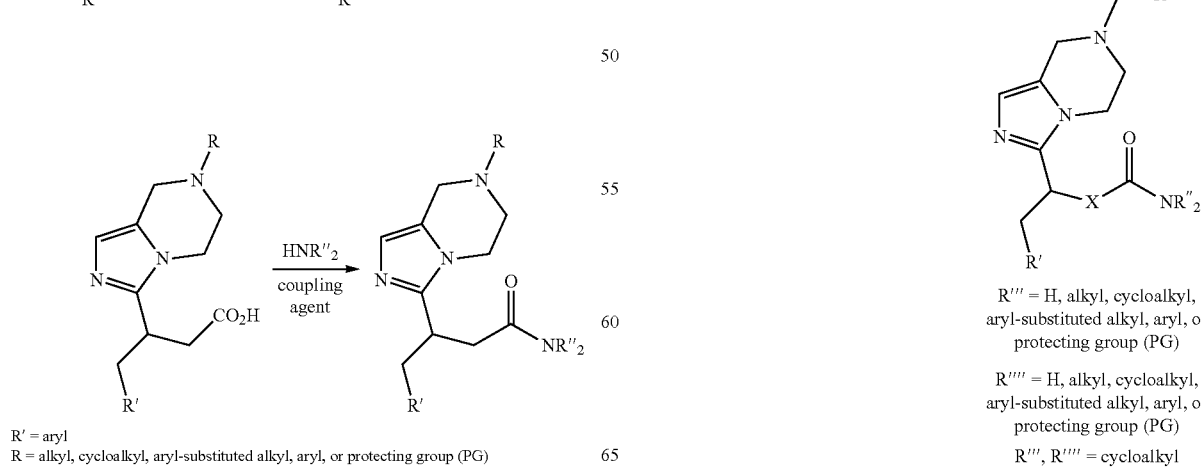

R' = aryl
X = O, NH, CH₂

R' = aryl
R = alkyl, cycloalkyl, aryl-substituted alkyl, aryl, or protecting group (PG)

R''' = H, alkyl, cycloalkyl, aryl-substituted alkyl, aryl, or protecting group (PG)

R'''' = H, alkyl, cycloalkyl, aryl-substituted alkyl, aryl, or protecting group (PG)

R''', R'''' = cycloalkyl

Scheme 14.

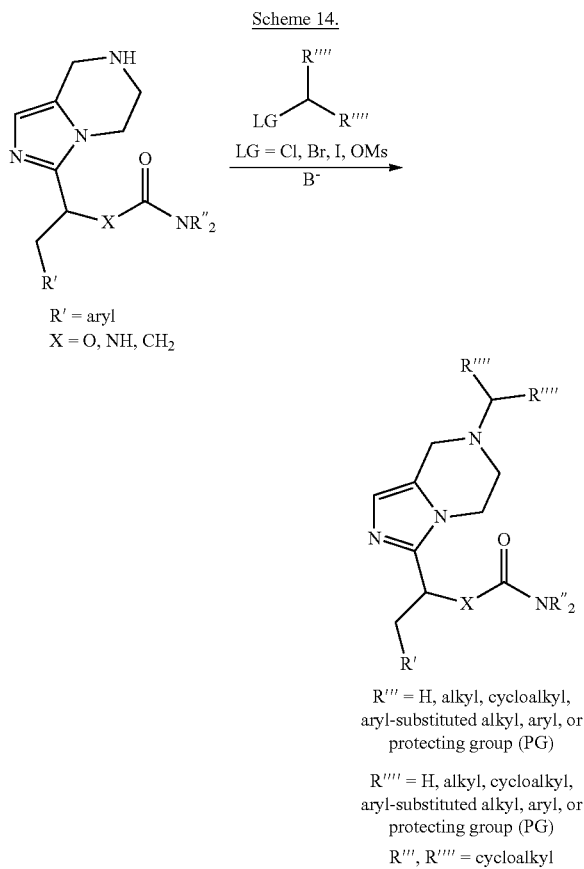

Biological Methods

In vitro Pharmacology.

Tissue Culture. SK-N-MC cells were grown at 37° C. in 5% $CO_2$ as a monolayer in medium consisting of MEM with Earle's salts and L-glutamine (Invitrogen) supplemented with 10% fetal bovine serum (Invitrogen).

Membrane Preparation. Crude membranes were prepared from SK-N-MC cells expressing CGRP receptors. The cells were rinsed twice with phosphate-buffered saline (155 mM NaCl, 3.3 mM $Na_2HPO_4$, 1.1 mM $KH_2PO_4$, pH 7.4), and incubated for 5-10 min. at 4° C. in hypotonic lysis buffer consisting of 10 mM Tris (pH 7.4) and 5 mM EDTA. The cells were transferred from plates to polypropylene tubes (16×100 mm) and homogenized using a polytron. Homogenates were centrifuged at 32,000×g for 30 min. The pellets were resuspended in cold hypotonic lysis buffer with 0.1% mammalian protease inhibitor cocktail (Sigma) and assayed for protein concentration. The SK-N-MC homogenate was aliquoted and stored at −80° C.

Radioligand Binding Assay. The compounds of invention were solubilized and carried through serial dilutions using 100% DMSO. Aliquots from the compound serial dilutions were further diluted 25 fold into assay buffer (50 mM Tris-Cl pH 7.5, 5 mM $MgCl_2$, 0.005% Triton X-100) and transferred (volume 50 µl) into 96 well assay plates. [$^{125}$I]-CGRP (GE Healthcare or Perkin-Elmer) was diluted to 72 pM in assay buffer and a volume of 50 µl was added to each well. SK-N-MC membranes were thawed, diluted in assay buffer with fresh 0.1% mammalian protease inhibitor cocktail (Sigma), and re-homogenized. SK-N-MC homogenate (7 µg/well) was added in a volume of 100 µl. The assay plates were then incubated at room temperature for 2 h. Assays were stopped by addition of excess cold wash buffer (50 mM Tris-Cl pH 7.5, 0.1% BSA) immediately followed by filtration over glass fiber filters (Whatman GF/B) previously soaked in 0.5% PEI. Non-specific binding was defined with 1 µM beta-CGRP (Bachem). Protein bound radioactivity was determined using a gamma or scintillation counter. The resulting data was analyzed using a four parameter competitive binding equation (XLfit v2.0) and the $IC_{50}$ was defined as the concentration of a compound of invention required to displace 50% of radioligand binding. Final assay concentration of [$^{125}$I]-CGRP was 18 pM. The mean Kd for [$^{125}$I]-CGRP is 25.4 pM. All compounds of invention were evaluated in at least two separate experiments. See table 1 for data summary.

TABLE 1

| | Human CGRP Binding |
| --- | --- |
| Example | Human CGRP Receptor $IC_{50}$ (nM) |
| 1 | 0.26 |
| 2 | 1.70 |
| 3 | 2.95 |
| 4 | 0.22 |

Pharmaceutical Compositions and Methods of Treatment

The compounds of Formula I inhibit the CGRP receptor. As such, they are useful for treating conditions or disorders associated with aberrant CGRP levels or where modulating CGRP levels may have therapeutic benefit.

Accordingly, another aspect of the invention is a pharmaceutical composition comprising a compound of Formula I with a pharmaceutically acceptable adjuvant, carrier, or diluent.

Compounds are generally given as pharmaceutical compositions comprised of a therapeutically effective amount of a compound of Formula I, or a pharmaceutically acceptable salt, and a pharmaceutically acceptable carrier and may contain conventional exipients. A therapeutically effective amount is the amount needed to provide a meaningful patient benefit as determined by practitioners in that art. Pharmaceutically acceptable carriers are those conventionally known carriers having acceptable safety profiles. Compositions encompass all common solid and liquid forms including capsules, tablets, losenges, and powders as well as liquid suspensions, syrups, elixers, and solutions. Solid compositions may by formed in timed or sustained released formulations. Compositions are made using common formulation techniques and conventional excipients (such as binding and wetting agents) and vehicles (such as water and alcohols).

Solid compositions are normally formulated in dosage units providing from about 1 to about 1000 mg of the active ingredient per dose. Some examples of solid dosage units are 0.1 mg, 1 mg, 10 mg, 100 mg, 500 mg, and 1000 mg. Liquid compositions are generally in a unit dosage range of 1-100 mg/mL. Some examples of liquid dosage units are 0.1 mg/mL, 1 mg/mL, 10 mg/mL, 25 mg/mL, 50 mg/mL, and 100 mg/mL.

The invention encompasses all conventional modes of administration including oral, parenteral, intranasal, sublingual, and transdermal methods. Typically, the daily dose will be 0.01-100 mg/kg body weight daily. Generally, more compound is required orally and less parenterally. The specific dosing regime, however, should be determined by a physician using sound medical judgement.

Inhibitors at the receptor level to CGRP are postulated to be useful in pathophysiologic conditions where excessive CGRP receptor activation has occurred. Some of these include neurogenic vasodilation, neurogenic inflammation, migraine, cluster headache and other headaches, thermal injury, circulatory shock, menopausal flushing, and asthma. CGRP receptor activation has been implicated in the pathogenesis of migraine headache (Edvinsson L. CNS Drugs 2001, 15(10),745-53; Williamson, D. J. Microsc. Res. Tech. 2001, 53, 167-178.; Grant, A. D. Brit. J. Pharmacol. 2002, 135, 356-362.). Serum levels of CGRP are elevated during migraine (Goadsby P. J. et al. Ann. Neurol. 1990, 28, 183-7) and treatment with anti-migraine drugs returns CGRP levels to normal coincident with alleviation of headache (Gallai V. et al. Cephalalgia 1995, 15, 384-90). Migraineurs exhibit elevated basal CGRP levels compared to controls (Ashina M. et al., Pain 2000, 86(1-2), 133-8). Intravenous CGRP infusion produces lasting headache in migraineurs (Lassen L. H. et al. Cephalalgia. 2002, 22(1), 54-61). Preclinical studies in dog and rat report that systemic CGRP blockade with the peptide antagonist CGRP(8-37) does not alter resting systemic hemodynamics nor regional blood flow (Shen, Y-T. et al. J. Pharmacol. Exp. Ther. 2001, 298, 551-8). Thus, CGRP-receptor antagonists may present a novel treatment for migraine that avoids the cardiovascular liabilities of active vasoconstriction associated with non-selective 5-HT1B/1D agonists, "triptans" (e.g., sumatriptan).

Another aspect of the invention is a method of inhibiting the CGRP receptor comprising contacting the CGRP receptor with a compound of formula I or a pharmaceutically acceptable salt thereof.

Another aspect of the invention is a method for treating conditions associated with aberrant levels of CGRP comprising the administration of a therapeutically effective amount of a compound of formula I to a patient.

Another aspect of the invention is the use of a compound of formula I in the manufacture of a medicament for the treatment of conditions related to aberrant levels of CGRP.

Another aspect of the invention is a method of treating migraine or headache.

Another aspect of the invention relates to a method of treating inflammation (particularly neurogenic inflammation), pain, thermal injury, circulatory shock, diabetes, Reynaud's syndrome, peripheral arterial insufficiency, subarachnoid/cranial hemorrhage, tumor growth, flushing associated with menopause and other conditions the treatment of which can be effected by the antagonism of the CGRP receptor by the administration of pharmaceutical compositions comprising compounds of Formula (I) as defined herein.

Another aspect of the invention relates to methods selected from the group consisting of (a) immune regulation in gut mucosa (b) protective effect against cardiac anaphylactic injury (c) stimulating or preventing interleukin-1b(IL-1b)-stimulation of bone resorption (d) modulating expression of NK1 receptors in spinal neurons and (e) airway inflammatory diseases and chronic obstructive pulmonary disease including asthma. See (a) Calcitonin Receptor-Like Receptor Is Expressed on Gastrointestinal Immune Cells. Hagner, Stefanie; Knauer, Jens; Haberberger, Rainer; Goeke, Burkhard; Voigt, Karlheinz; McGregor, Gerard Patrick. Institute of Physiology, Philipps University, Marburg, Germany. Digestion (2002), 66(4), 197-203; (b) Protective effects of calcitonin gene-related peptide-mediated evodiamine on guinea-pig cardiac anaphylaxis. Rang, Wei-Qing; Du, Yan-Hua; Hu, Chang-Ping; Ye, Feng; Tan, Gui-Shan; Deng, Han-Wu; Li, Yuan-Jian. School of Pharmaceutical Sciences, Department of Pharmacology, Central South University, Xiang-Ya Road 88, Changsha, Hunan, Naunyn-Schmiedeberg's Archives of Pharmacology (2003), 367(3), 306-311; (c) The experimental study on the effect calcitonin gene-related peptide on bone resorption mediated by interleukin-1 Lian, Kai; Du, Jingyuan; Rao, Zhenyu; Luo, Huaican. Department of Orthopedics, Xiehe Hospital, Tongji Medical College, Huazhong University of Science and Technology, Wuhan, Peop. Rep. China. Journal of Tongji Medical University (2001), 21(4), 304-307, (d) Calcitonin gene-related Peptide regulates expression of neurokinin) receptors by rat spinal neurons. Seybold V S, McCarson K E, Mermelstein P G, Groth R D, Abrahams L G. J. Neurosci. 2003 23 (5): 1816-1824. epartment of Neuroscience, University of Minnesota, Minneapolis, Minn. 55455, and Department of Pharmacology, Toxicology, and Therapeutics, University of Kansas Medical Center, Kansas City, Kans. 66160 (e) Attenuation of antigen-induced airway hyperresponsiveness in CGRP-deficient mice. Aoki-Nagase, Tomoko; Nagase, Takahide; Oh-Hashi, Yoshio; Shindo, Takayuki; Kurihara, Yukiko; Yamaguchi, Yasuhiro; Yamamoto, Hiroshi; Tomita, Tetsuji; Ohga, Eijiro; Nagai, Ryozo; Kurihara, Hiroki; Ouchi, Yasuyoshi. Department of Geriatric Medicine, Graduate School of Medicine, University of Tokyo, Tokyo, Japan. American Journal of Physiology (2002), 283(5,Pt. 1), L963-L970; (f) Calcitonin gene-related peptide as inflammatory mediator. Springer, Jochen; Geppetti, Pierangelo; Fischer, Axel; Groneberg, David A. Charite Campus-Virchow, Department of Pediatric Pneumology and Immunology, Division of Allergy Research, Humboldt-University Berlin, Berlin, Germany. Pulmonary Pharmacology & Therapeutics (2003), 16(3), 121-130; and (g) Pharmacological targets for the inhibition of neurogenic inflammation. Helyes, Zsuzsanna; Pinter, Erika; Nemeth, Jozsef; Szolcsanyi, Janos. Department of Pharmacology and Pharmacotherapy, Faculty of Medicine, University of Pecs, Pecs, Hung. Current Medicinal Chemistry: Anti-Inflammatory & Anti-Allergy Agents (2003), 2(2), 191-218.

Another aspect of this invention relates to a method of treatment using combinations of Formula I compounds with one or more agents selected from the group consisting of COX-2 inhibitors, NSAIDS, aspirin, acetaminophen, triptans, ergotamine and caffeine for the treatment of migraine.

"Migraine," "headache," and related terms are as understood by medical practitioners. Migraine encompasses all classes of migraine including common, classic, cluster, fulgurating, hemiplegic, opthalmoplegic, and opthomalmic.

"Therapeutically effective" means there is a meaningful patient benefit as understood by medical practitioners.

"Patient" means a person who may benefit from treatment as determined by medical practitioners.

DESCRIPTION OF SPECIFIC EMBODIMENTS

The following experimental procedures describe the synthesis of some Formula I compounds. Standard chemistry conventions are used in the text unless otherwise noted. The experimental encompass reasonable variations known in the art. The following HPLC conditions may be used where indicated.

Abbreviations used in the schemes generally follow conventions used in the art. Chemical abbreviations used in the specification and examples are defined as follows: "NaHMDS" for sodium bis(trimethylsilyl)amide; "DMF" for N,N-dimethylformamide; "MeOH" for methanol; "NBS" for N-bromosuccinimide; "Ar" for aryl; "TFA" for trifluoroacetic acid; "LAH" for lithium aluminum hydride; "BOC" for t-butoxycarbonyl, "DMSO" for dimethylsulfoxide; "h" for hours; "rt" for room temperature or retention time (context will dictate); "min" for minutes; "EtOAc" for ethyl acetate; "THF" for tetrahydrofuran; "EDTA" for ethylenediaminetetraacetic acid; "Et$_2$O" for diethyl ether; "DMAP" for 4-dimethylaminopyridine; "DCE" for 1,2-dichloroethane; "ACN" for acetonitrile; "DME" for 1,2-dimethoxyethane; "HOBt" for 1-hydroxybenzotriazole hydrate; "DIEA" for diisopropylethylamine, "Nf" for CF$_3$(CF$_2$)$_3$SO$_2$—; and "TMOF" for trimethylorthoformate.

Abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "µL" for microliter or microliters, "N" for normal, "M" for molar, "mmol" for millimole or millimoles, "min" for minute or minutes, "h" for hour or hours, "rt" for room temperature, "RT" for retention time, "atm" for atmosphere, "psi" for pounds per square inch, "conc." for concentrate, "sat" or "sat'd" for saturated, "MW" for molecular weight, "mp" for melting point, "ee" for enantiomeric excess, "MS" or "Mass Spec" for mass spectrometry, "ESI" for electrospray ionization mass spectroscopy, "HR" for high resolution, "HRMS" for high resolution mass spectrometry , "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "$^1$H" for proton, "δ" for delta, "s" for singlet, "d" for doublet, "t" for triplet, "q" for quartet, "m" for multiplet, "br" for broad, "Hz" for hertz, and "α", "β", "R", "S", "E", and "Z" are stereochemical designations familiar to one skilled in the art.

Analytical HPLC method 1: Phenomenex 4.6×50 mm C18 10 um, A=90% H$_2$O/10% MeOH, B=90% MeOH/10% H$_2$O, Modifier 0.1% TFA, 0.00 min=0% B, 3.0 min=100% B, 4.0 min=100% B, Flow rate=4 mL/min.

Analytical HPLC method 2: Phenomenex 4.6×50 mm C18 10 um, A=90% H$_2$O/10% MeOH, B=90% MeOH/10% H$_2$O, Modifier 0.1% TFA, 0.00 min=0% B, 3.0 min=100% B, 3.0 min=100% B, Flow rate=4 mL/min.

Intermediate 1

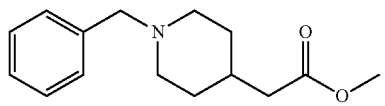 [SMILES: COC(=O)CC1CCN(Cc2ccccc2)CC1]

Methyl 2-(1-benzylpiperidin-4-yl)acetate. Sodium hydride (60% in mineral oil, 10.55 g, 264 mmol) was washed with hexanes then suspended in N,N-dimethylformamide (200 mL). Mixture was cooled to 0° C. Trimethyl phosphonoacetate (38.0 mL, 249 mmol) was added to the mixture dropwise. The reaction was stirred at 0° C. for 30 minutes. 1-Benzyl-4-piperidone (40.0 mL, 220 mmol) was added to the reaction mixture dropwise. The reaction was warmed to ambient temperature and held with stirring for 1 h. The reaction mixture was diluted with diethyl ether (500 mL), washed with water (2×), then brine. The organic layer was dried (magnesium sulfate), filtered, and concentrated in vacuo. The residue was dissolved in methanol (220 mL). Platinum(IV) oxide (600 mg, 2.64 mmol) was added to the mixture. The reaction vessel was placed on a Parr apparatus, charged with 40 psi of hydrogen gas, and shaken at room temperature for 5 h. The reaction mixture was removed from the apparatus, filtered through celite, and concentrated. The residue was passed through a short column of silica gel eluting with ethyl acetate. Fractions were concentrated in vacuo. The title compound was obtained as amber oil in 90% yield. $^1$H NMR (300 MHz, CDCl$_3$): δ 7.31-7.16 (m, 5H), 3.62 (s, 3H), 3.45 (s, 2H), 2.83 (d, J=11.71, 2H), 2.20 (d, J=6.95, 2H), 2.00-1.88 (m, 1H), 1.82-1.69 (m, 1H), 1.69-1.59 (m, 2H), 1.38-1.25 (m, 2H). Mass spec.: 249.3 (MH)$^+$.

Intermediate 2

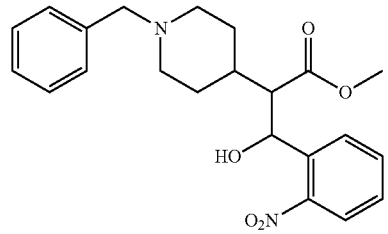 [SMILES: COC(=O)C(C1CCN(Cc2ccccc2)CC1)C(O)c1ccccc1[N+](=O)[O-]]

(±)-Methyl 2-(1-benzylpiperidin-4-yl)-3-hydroxy-3-(2-nitrophenyl)propanoate. Diisopropylamine (3.50 mL, 24.9 mmol) was dissolved in tetrahydrofuran (30 mL). The mixture was cooled to −78° C. Butyllithium (2.5 M in pentane, 9.8 mL, 24.5 mmol) was added to the mixture dropwise, and the reaction stirred at −78° C. for 15 min. A solution of methyl 2-(1-benzylpiperidin-4-yl)acetate (5.50 g, 22.2 mmol) in THF (8 mL) was then added to the mixture dropwise over 20 minutes. The mixture was stirred at −78° C. for 45 minutes. A solution of 2-nitrobenzaldehyde (3.70 g, 24.5 mmol) in THF (5 mL) was then added to the mixture dropwise over 15 minutes. The reaction was stirred at −78° C. for 30 minutes and quenched by the addition of saturated aqueous ammonium chloride. The resulting mixture was warmed to room temperature, extracted with ethyl acetate (2×). The combined organics were dried (magnesium sulfate), filtered, and concentrated. Silica gel chromatography afforded the desired product in 89% yield as light yellow foam. Mass spec.: 399.3 (MH)$^+$.

Intermediate 3

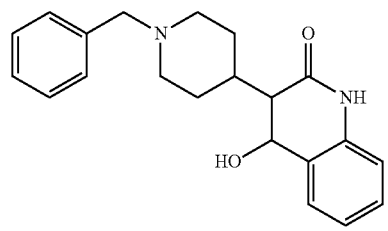 [SMILES: O=C1Nc2ccccc2C(O)C1C1CCN(Cc2ccccc2)CC1]

(±)-3-(1-Benzylpiperidin-4-yl)-4-hydroxy-3,4-dihydroquinolin-2(1H)-one. (±)-Methyl 2-(1-benzylpiperidin-4-yl)-3-hydroxy-3-(2-nitrophenyl)propanoate (950 mg, 2.4 mmol) was dissolved in acetic acid (20 mL). Iron(0) (1.0 g, 17.7 mmol) was added to the mixture. The reaction was heated at 85° C. and held with stirring for 1.5 h. The mixture was cooled to room temperature and diluted with water (30 mL). The liquid was decanted away from the solids. The aqueous solution was concentrated in vacuo. The residue was treated with ethyl acetate (50 mL). The mixture was made basic with aqueous sodium hydroxide. Celite was added to the resulting suspension to create a slurry which was in turn was filtered. The filtrate layers were separated. The aqueous layer was extracted with ethyl acetate. Combined organic layers were dried (magnesium sulfate), filtered, and concentrated in vacuo. The title compound was obtained without further purification as yellow oil in 69% yield. Mass spec.: 335.3 (MH)$^+$.

Intermediate 4

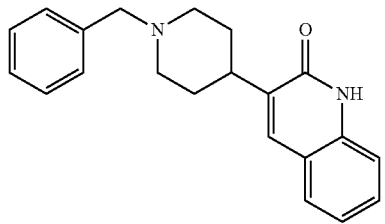 [SMILES: O=c1[nH]c2ccccc2cc1C1CCN(Cc2ccccc2)CC1]

3-(1-Benzylpiperidin-4-yl)quinolin-2(1H)-one. (±)-3-(1-Benzylpiperidin-4-yl)-4-hydroxy-3,4-dihydroquinolin-2(1H)-one (550 mg, 1.6 mmol) was suspended in benzene (10 mL). p-Toluenesulfonic acid monohydrate (370 mg, 1.9 mmol) was added to the mixture. The reaction was heated to reflux and held there for 1 h. The reaction mixture was concentrated in vacuo. The resulting residue was dissolved in 10% ethanol/dichloromethane (50 mL) and washed with aqueous sodium bicarbonate (2×). The organic layer was dried (magnesium sulfate), filtered, and concentrated in vacuo. The residue was triturated with diethyl ether to give a solid which was filtered, washed with diethyl ether, and dried in vacuo. The title compound was obtained as off-white solid in 63% yield. $^1$H NMR (300 MHz, DMSO-d6): δ 11.72 (s, 1H), 7.72 (s, 1H), 7.62 (d, J=6.95, 1H), 7.47-7.38 (m, 1H), 7.35-7.30 (m, 4H), 7.29-7.20 (m, 2H), 7.14 (t, J=7.50, 1H), 3.49 (s, 3H), 2.92 (d, J=11.34, 2H), 2.83-2.69 (m, 1H), 2.04 (t, J=10.61, 2H), 1.78 (d, J=12.08, 2H), 1.71-1.47 (m, 2H). Mass spec.: 319.3 (MH)$^+$.

Intermediate 5

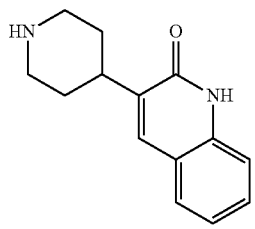 [SMILES: O=c1[nH]c2ccccc2cc1C1CCNCC1]

3-(Piperidin-4-yl)quinolin-2(1H)-one. 3-(1-Benzylpiperidin-4-yl)quinolin-2(1H)-one (1.72 g, 5.40 mmol) was suspended in methanol (70 mL). A catalytic amount of palladium hydroxide (20% on carbon) was added to the mixture. The reaction vessel was placed on a Parr apparatus and charged with 55 psi of hydrogen. The reaction was shaken at room temperature for 5 h. The mixture was removed from the apparatus and filtered. The filtrate was concentrated to give the title compound as white solid in 90% yield. $^1$H NMR (300 MHz, DMSO-d6): δ 7.65 (s, 1H), 7.64 (d, J=10.61, 1H), 7.41 (t, J=7.50, 1H), 7.26 (d, J=8.05, 1H), 7.13 (t, J=7.32, 1H), 3.02 (d, J=11.71, 2H), 2.82 (t, J=11.89, 2H), 2.58 (t, J=11.71, 2H), 1.73 (t, J=11.71, 2H), 1.42 (m, 2H). Mass spec.: 229.4 (MH)$^+$.

Intermediate 6

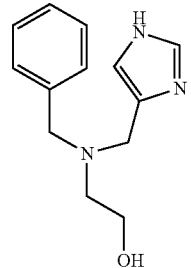 [SMILES: OCCN(Cc1ccccc1)Cc1c[nH]cn1]

2-(((1H-Imidazol-4-yl)methyl)(benzyl)amino)ethanol. A flask was charged with 1H-imidazole-4-carbaldehyde (5.0 g, 52 mmol), tetrahydrofuran (75 mL), and 2-(benzylamino)ethanol (9.44 g, 62.4 mmol). The reaction was stirred at room temperature for 1 h. To this was added sodium triacetoxyborohydride (13.2 g, 62.4 mmol) in one portion. A significant exotherm was noted. After 10 min, the solution had become a thick suspension which required occasional agitation by hand. The reaction was stirred at room temperature overnight. The reaction was concentrated, dissolved in water (100 mL), made basic with an aqueous solution of potassium carbonate, and extracted into dichloromethane (3×). The organics were dried over potassium carbonate and concentrated. Column chromatography (5% MeOH/DCM→10% MeOH/DCM→90:10:1 DCM/MeOH/2M ammonia in methanol) gave 10.2 g (85%) as a viscous oil. Mass spec.: 232.11 (MH)$^+$.

Intermediate 7

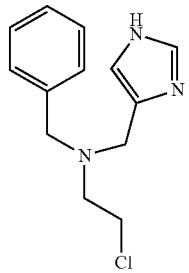

2HCl

N-((1H-Imidazol-4-yl)methyl)-N-benzyl-2-chloroethanamine.2HCl. To a stirred solution of 2-(((1H-imidazol-4-yl)methyl)(benzyl)amino)ethanol (10.2 g, 44 mmol) in dichloromethane (200 mL) at room temperature was added thionyl chloride (12.9 mL, 176 mmol) over 20 min. The resulting heterogeneous, gummy mixture was heated to reflux, occasionally agitating manually. The reaction was heated at reflux with stirring, for 3 h, cooled to room temperature, and stirred at room temperature overnight. The reaction was concentrated to give a white solid. To this was added acetonitrile, and the reaction re-concentrated. The crude product (quant.) was used without purification. Mass spec.: 250.02 (MH)+.

Intermediate 8

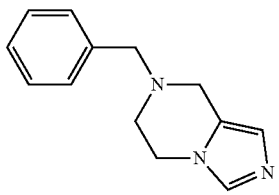 [SMILES: c1ccc(CN2CCn3cncc3C2)cc1]

7-Benzyl-5,6,7,8-tetrahydroimidazo[1,5-a]pyrazine. To a suspension of N-((1H-imidazol-4-yl)methyl)-N-benzyl-2-chloroethanamine.2HCl (14.23 g, 44 mmol) in acetonitrile (250 mL) was added triethylamine (22.1 mL, 159 mmol) dropwise via an addition funnel over 30 min. After addition was complete, the reaction was slowly warmed to reflux and held there for 2 h. The reaction was cooled to room temperature and stirred overnight. The reaction was filtered to remove solids and concentrated. The resulting risidue was filtered through basic alumina, using 10% MeOH/DCM as eluent. The eluent was concentrated, and the resulting residue purified by column chromatography (5% MeOH/DCM→10% MeOH/DCM) to give 2.88 g (31%) as a white crystalline solid. ¹H NMR (CHLOROFORM-d) δ: 7.51 (br. s., 1H), 7.26-7.40 (m, 5H), 6.75 (s, 1H), 4.05 (t, J=5.5 Hz, 2H), 3.68 (d, J=16.8 Hz, 4H), 2.84 (t, J=5.6 Hz, 2H). ¹³C NMR (CHLOROFORM-d) δ: 137.5, 134.9, 129.1, 128.6, 127.6, 126.2, 122.7, 62.2, 49.8, 49.1, 43.0. Mass spec.: 214.08 (MH)+.

Intermediate 9

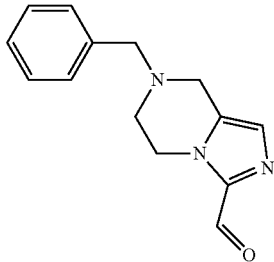 [SMILES: O=Cc1ncc2n1CCN(Cc1ccccc1)C2]

7-Benzyl-5,6,7,8-tetrahydroimidazo[1,5-a]pyrazine-3-carbaldehyde. To a solution of 7-benzyl-5,6,7,8-tetrahydroimidazo[1,5-a]pyrazine (2.0 g, 9.4 mmol) in tetrahydrofuran (15 mL) at −78 C was added n-butyllithium (1.6 M in hexanes, 6.5 mL, 10.3 mmol). The reaction was warmed to 0 C, stirred for 15 min, recooled to −78 C, and treated with dimethylformamide (1.45 mL, 18.8 mmol). The reaction was allowed to warm to 0C, quenched by addition of saturated ammonium chloride, and concentrated to remove most of the tetrahydrofuran. The reaction was extracted into ethyl acetate. The organics were washed with water, then brine, dried over MgSO4, and concentrated. Column chromatography gave 1.80 g (80%) as an off-white solid. ¹H NMR (CHLOROFORM-d) δ: 9.72 (s, 1H), 7.27-7.43 (m, 5H), 7.02 (s, 1H), 4.46 (br. s., 2H), 3.75 (br. s., 4H), 2.92 (br. s., 2H). ¹³C NMR (CHLOROFORM-d) δ: 181.3, 142.8, 129.0, 128.6, 127.8, 127.3, 61.9, 49.1, 48.5, 44.7. Mass spec.: 242.03 (MH)+.

Intermediate 10

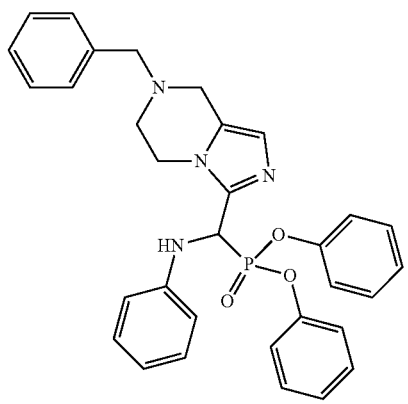 [SMILES: O=P(Oc1ccccc1)(Oc1ccccc1)C(Nc1ccccc1)c1ncc2n1CCN(Cc1ccccc1)C2]

(±)-Diphenyl(7-benzyl-5,6,7,8-tetrahydroimidazo[1,5-a]pyrazin-3-yl)(phenylamino)methylphosphonate. To a solution of 7-benzyl-5,6,7,8-tetrahydroimidazo[1,5-a]pyrazine-3-carbaldehyde (1.80 g, 7.5 mmol) in isopropyl alcohol (15 mL) was added aniline (0.82 mL, 9.0 mmol) followed by diphenylphosphite (2.29 mL, 11.9 mmol). The resulting solution was stirred for 15 min and then allowed to stand overnight. In the morning, a precipitate had formed. The precipitate was filtered, crushed with a spatula, washed with cold isopropyl alcohol, then ether, air dried, and pumped on high vacuum to give 3.50 g (85%) as a white powder. ¹H NMR (CHLOROFORM-d) δ: 7.22-7.34 (m, 9H), 7.09-7.19 (m, 6H), 7.01 (d, J=7.9 Hz, 2H), 6.74-6.80 (m, 4H), 5.42 (d, J=15.6 Hz, 1H), 5.07 (br. s., 1H), 4.07-4.21 (m, 2H), 3.60 (s, 3H), 3.46 (d, J=14.3 Hz, 1H), 2.74-2.83 (m, 1H), 2.54-2.62 (m, 1H).

Intermediate 11

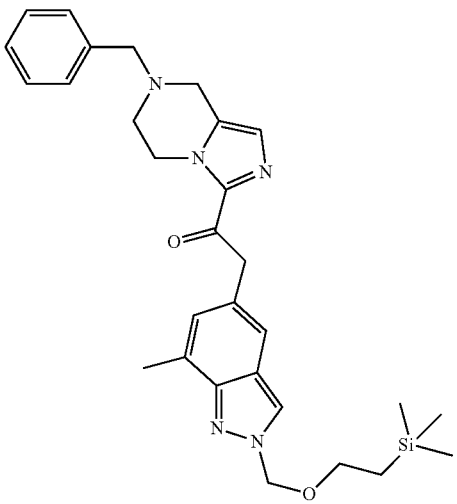 [SMILES: Cc1cc(CC(=O)c2ncc3n2CCN(Cc2ccccc2)C3)cc2cn(COCC[Si](C)(C)C)nc12]

1-(7-Benzyl-5,6,7,8-tetrahydroimidazo[1,5-a]pyrazin-3-yl)-2-(7-methyl-2-((2-(trimethylsilyl)ethoxy)methyl)-2H-indazol-5-yl)ethanone. To a suspension of (±)-diphenyl(7-benzyl-5,6,7,8-tetrahydroimidazo[1,5-a]pyrazin-3-yl)(phenylamino)methylphosphonate (2.30 g, 4.2 mmol) and 7-methyl-2-((2-(trimethylsilyl)ethoxy)methyl)-2H-indazole-5-carbaldehyde(Luo, G., et al, J. Org. Chem. 2006, 5392-5395) (1.21 g, 4.2 mmol) in tetrahydrofuran (9.2 mL) and isopropyl alcohol (2.3 mL) was added cesium carbonate (1.77 g, 5.4 mmol) in one portion. The reaction was stirred at room temperature overnight. In the morning, the reaction had stopped stirring. After getting it stirring again, the reaction was stirred an additional 2 h. The suspension was cooled to 0 C, and treated with 1 N HCl (14 mL) dropwise. The ice bath was removed and the reaction stirred at room temperature for 2 h. The reaction was diluted with ether and water. The aqueous was extracted with ether (2×). The ethereal was concentrated. Column chromatography (50% EtOAc/Hex→100% EtOAc) gave 525 mg (24%) as a foam. $^1$H NMR (CHLOROFORM-d) δ: 7.46 (s, 1H), 7.27-7.41 (m, 6H), 7.05 (s, 1H), 6.97 (s, 1H), 5.70 (s, 2H), 4.44 (br. s., 2H), 4.39 (s, 2H), 3.71 (br. s., 4H), 3.55-3.63 (m, 2H), 2.86 (br. s., 2H), 2.59 (s, 3H), 0.89-0.96 (m, 2H), −0.04 (s, 9H). Mass spec.: 516.61 (MH)$^+$.

Intermediate 12

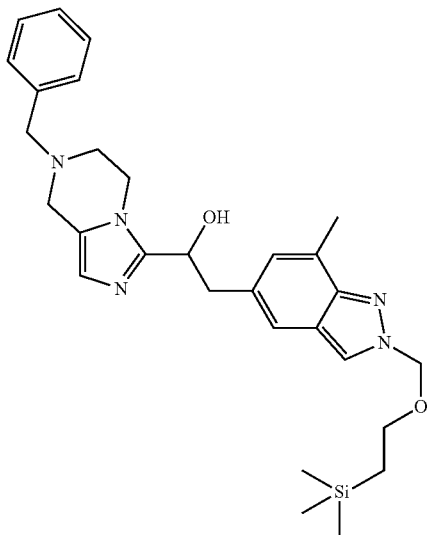 [SMILES: Cc1cc(CC(O)c2ncc3n2CCN(Cc2ccccc2)C3)cc2cn(COCC[Si](C)(C)C)nc12]

(±)-1-(7-Benzyl-5,6,7,8-tetrahydroimidazo[1,5-a]pyrazin-3-yl)-2-(7-methyl-2-((2-(trimethylsilyl)ethoxy)methyl)-2H-indazol-5-yl)ethanol. To a solution of 1-(7-benzyl-5,6,7,8-tetrahydroimidazo[1,5-a]pyrazin-3-yl)-2-(7-methyl-2-((2-(trimethylsilyl)ethoxy)methyl)-2H-indazol-5-yl)ethanone (400 mg, 0.78 mmol) in ethanol (8 mL) at room temperature was added sodium borohydride (59 mg, 1.6 mmol). After 30 min, the reaction was cooled to 0C and quenched by the dropwise addition of saturated ammonium chloride until no further gas evolved. The reaction was concentrated to remove most of the ethanol. The resulting residue was suspended in water and extracted with ethyl acetate. The organics were washed with brine, dried over MgSO4, and concentrated to give 390 mg (97%) as a white foam which was used without purification. Mass spec.: 518.25 (MH)$^+$.

Intermediate 13

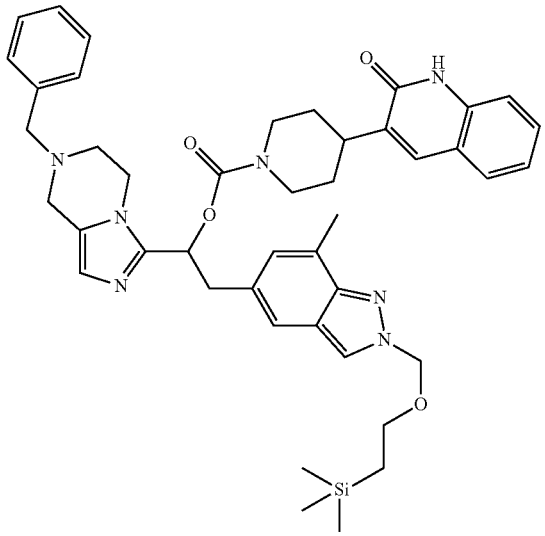 [SMILES: Cc1cc(CC(OC(=O)N2CCC(c3cc4ccccc4[nH]c3=O)CC2)c2ncc3n2CCN(Cc2ccccc2)C3)cc2cn(COCC[Si](C)(C)C)nc12]

(±)-1-(7-Benzyl-5,6,7,8-tetrahydroimidazo[1,5-a]pyrazin-3-yl)-2-(7-methyl-2-((2-(trimethylsilyl)ethoxy)methyl)-2H-indazol-5-yl)ethyl 4-(2-oxo-1,2-dihydroquinolin-3-yl)piperidine-1-carboxylate. To a solution of 3-(piperidin-4-yl)quinolin-2(1H)-one (668 mg, 2.9 mmol) and triethylamine (0.41 mL, 2.9 mmol) in dimethylformamide (10 mL) at room temperature was added 4-nitrophenylchloroformate (590 mg, 2.9 mmol) in two portions. After stirring for 30 min, the resulting suspension was slowly poured into a vigorously stirred flask of water (100 mL). The resulting solid was collected by filtration, air dried, and pumped on high vacuum to give 990 mg (86%) of 4-nitrophenyl 4-(2-oxo-1,2-dihydroquinolin-3-yl)piperidine-1-carboxylate as a light yellow solid which was used without purification.

To a suspension of (±)-1-(7-benzyl-5,6,7,8-tetrahydroimidazo[1,5-a]pyrazin-3-yl)-2-(7-methyl-2-((2-(trimethylsilyl)ethoxy)methyl)-2H-indazol-5-yl)ethanol (390 mg, 0.75 mmol) and 4-nitrophenyl 4-(2-oxo-1,2-dihydroquinolin-3-yl)piperidine-1-carboxylate (445 mg, 1.1 mmol) in tetrahydrofuran (10 mL) at room temperature was added sodium hydride (95%, 72 mg, 3.0 mmol) in one portion. The reaction was stirred at room temperature overnight. The reaction was poured into water and ethyl acetate and the layers separated. The organics were washed with saturated sodium bicarbonate, then brine, dried over magnesium sulfate, and concentrated. Column chromatography (100% EtOAc→10% MeOH/EtOAc) gave 365 mg (63%) as a colorless oil. Mass spec.: 772.43 (MH)$^-$.

Example 1

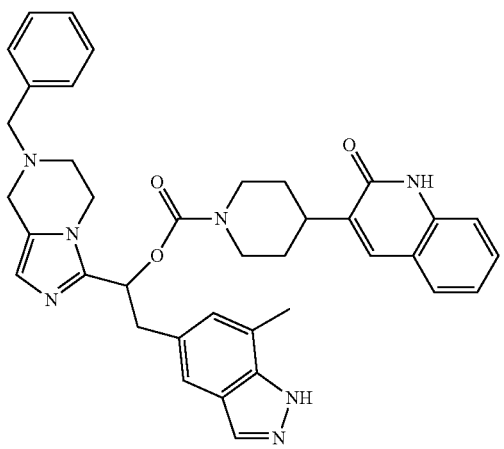 [SMILES: Cc1cc(CC(OC(=O)N2CCC(c3cc4ccccc4[nH]c3=O)CC2)c2ncc3n2CCN(Cc2ccccc2)C3)cc2cn[nH]c12]

(±)-1-(7-Benzyl-5,6,7,8-tetrahydroimidazo[1,5-c]pyrazin-3-yl)-2-(7-methyl-1H-indazol-5-yl)ethyl 4-(2-oxo-1,2-dihydroquinolin-3-yl)piperidine-1-carboxylate. (±)-1-(7-benzyl-5,6,7,8-tetrahydroimidazo[1,5-a]pyrazin-3-yl)-2-(7-methyl-2-((2-(trimethylsilyl)ethoxy)methyl)-2H-indazol-5-yl)ethyl 4-(2-oxo-1,2-dihydroquinolin-3-yl)piperidine-1-carboxylate (365 mg, 0.47 mmol) was dissolved in trifluoroacetic acid (50% in dichloromethane, 10 mL) at room temperature. After 2.5 h, the reaction was concentrated. The reaction was purified by column chromatography (5% MeOH/DCM→7.5% MeOH/DCM). The residue was re-purified by preparative HPLC. The resulting residue was passed through a shortp column of basic alumina (eluting with 10% MeOH/DCM to give 120 mg (40%) as a white foam solid. LC/MS (Analytical HPLC method 1): $t_r$=2.79 min; Mass spec.: 642.35 (MH)$^+$.

Example 2 and Example 3

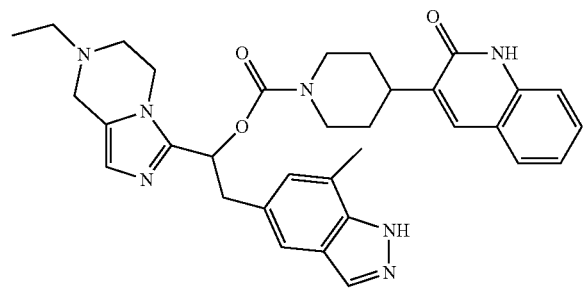

and

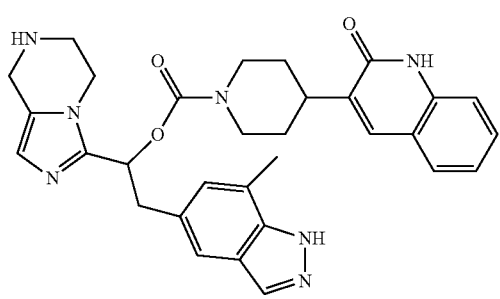

(±)-1-(7-Ethyl-5,6,7,8-tetrahydroimidazo[1,5-a]pyrazin-3-yl)-2-(7-methyl-1H-indazol-5-yl)ethyl 4-(2-oxo-1,2-dihydroquinolin-3-yl)piperidine-1-carboxylate and 2-(7-methyl-1H-indazol-5-yl)-1-(5,6,7,8-tetrahydroimidazo[1,5-a]pyrazin-3-yl)ethyl 4-(2-oxo-1,2-dihydroquinolin-3-yl)piperidine-1-carboxylate. A suspension of (±)-1-(7-benzyl-5,6,7,8-tetrahydroimidazo[1,5-a]pyrazin-3-yl)-2-(7-methyl-1H-indazol-5-yl)ethyl 4-(2-oxo-1,2-dihydroquinolin-3-yl)piperidine-1-carboxylate (75 mg, 0.12 mmol), palladium (10% on charcoal, 25 mg), and ammonium formate (74 mg, 1.2 mmol) in ethanol (3 mL) was heated at reflud for 2 h, occasionally knocking the sublimed ammonium formate back into the reaction with a spatula. The reaction was cooled, diluted with dichloromethane, filtered, and concentrated. Column chromatography (5% MeOH/DCM→20% MeOH/DCM) gave two fractions. The first to elute was (±)-1-(7-ethyl-5,6,7,8-tetrahydroimidazo[1,5-a]pyrazin-3-yl)-2-(7-methyl-1H-indazol-5-yl)ethyl 4-(2-oxo-1,2-dihydroquinolin-3-yl)piperidine-1-carboxylate (Example 2, 8.4 mg, 12%). LC/MS (Analytical HPLC method 2): $t_r$=1.91 min; Mass spec.: 580.31 (MH)$^+$. The second to elute was (±)-2-(7-methyl-1H-indazol-5-yl)-1-(5,6,7,8-tetrahydroimidazo[1,5-a]pyrazin-3-yl)ethyl 4-(2-oxo-1,2-dihydroquinolin-3-yl)piperidine-1-carboxylate (Example 3, 37 mg, 57%). LC/MS (Analytical HPLC method 2): $t_r$=1.80 min; Mass spec.: 552.34 (MH)$^+$.

Example 4

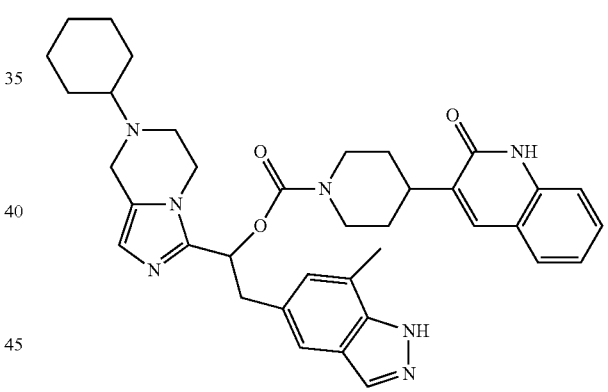

(±)-1-(7-Cyclohexyl-5,6,7,8-tetrahydroimidazo[1,5-a]pyrazin-3-yl)-2-(7-methyl-1H-indazol-5-yl)ethyl 4-(2-oxo-1,2-dihydroquinolin-3-yl)piperidine-1-carboxylate. To a solution of (±)-2-(7-methyl-1H-indazol-5-yl)-1-(5,6,7,8-tetrahydroimidazo[1,5-a]pyrazin-3-yl)ethyl 4-(2-oxo-1,2-dihydroquinolin-3-yl)piperidine-1-carboxylate (15 mg, 0.027 mmol) and cyclohexanone (5.7 µL, 0.054 mmol) in ethanol (1 mL) at room temperature was added sodium cyanoborohydride (3.4 mg, 0.054 mmol). After 5 min, one small drop of acetic acid was added. The reaction was treated with a second portion of cyclohexanone (5.7 µL, 0.054 mmol), followed by a second portion of sodium cyanoborohydride (3.4 mg, 0.054 mmol). After 30 min, the reaction was concentrated and purified by column chromatography (5%→10% MeOH/DCM) gave 11.3 mg (66%) as a white powder. LC/MS (Analytical HPLC method 2): $t_r$=1.99 min; Mass spec.: 634.36 (MH)$^+$.

The invention claimed is:

1. A compound of formula I

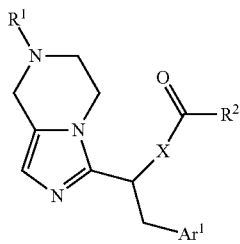

where:

R¹ is hydrogen, alkyl, cycloalkyl, or (Ar²)alkyl;

R² is piperidinyl, substituted with one substituent selected from the group consisting of

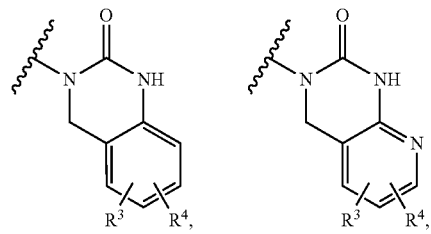

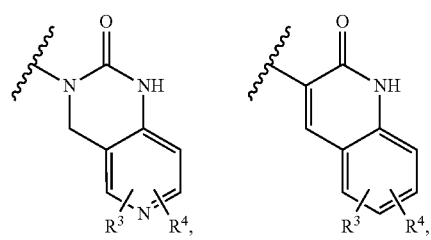

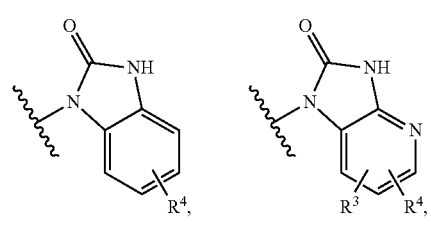

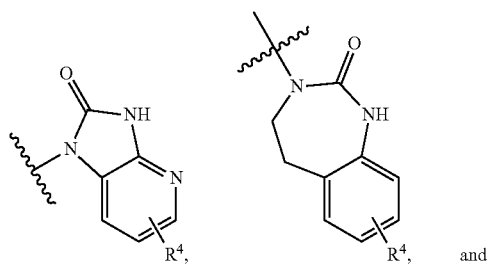

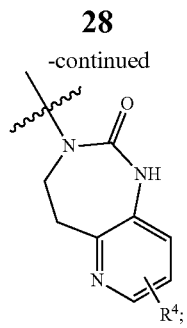

R³ is hydrogen, halo, cyano, alkyl, haloalkyl, alkoxy, or haloalkoxy;

R⁴ is hydrogen, halo, cyano, alkyl, haloalkyl, alkoxy, or haloalkoxy;

Ar¹ is indazolyl, optionally substituted with one substituent selected from the group consisting of halo, alkyl, and haloalkyl;

Ar² is phenyl, optionally substituted with one, two or three substituents selected from the group consisting of halo, alkyl, haloalkyl, alkoxy, and haloalkoxy; and X is O, CH₂, or NH;

or a pharmaceutically acceptable salt thereof.

2. The compound of claim 1, where R¹ is hydrogen, ethyl, cyclohexyl, or benzyl.

3. The compound of claim 1, where R² is piperidinyl, 4-substituted with one substituent selected from the group consisting of

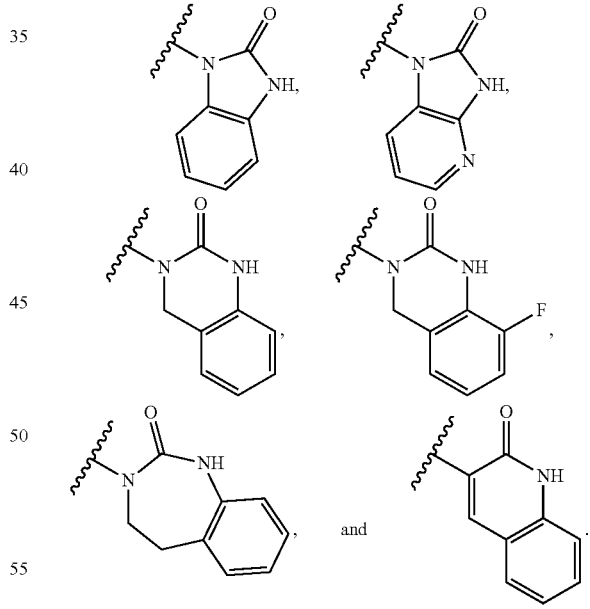

4. The compound of claim 1, where Ar¹ is indazolyl, substituted with one alkyl substituent.

5. The compound of claim 1, where Ar² is phenyl.

6. The compound of claim 1, where X is O.

7. The compound of claim 1, where:

R¹ is hydrogen, alkyl, cycloalkyl, or (Ar²)alkyl;

R² is piperidinyl, substituted with one substituent selected from the group consisting of

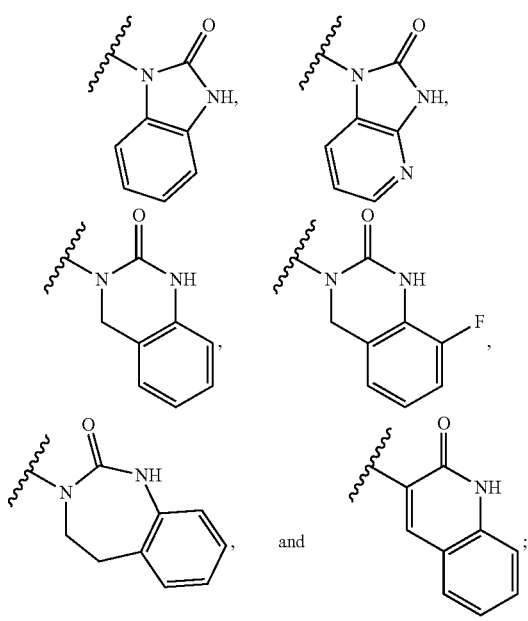

R³ is hydrogen;
R⁴ is hydrogen;
Ar¹ is indazolyl, substituted with one alkyl substituent;

Ar² is phenyl; and
X is O;
or a pharmaceutically acceptable salt thereof.

8. The compound of claim 1, where:
R¹ is hydrogen, ethyl, cyclohexyl, or benzyl;

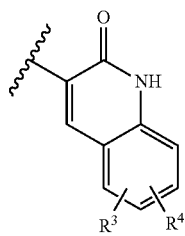

R² is piperidinyl, substituted with one substituent;
R³ is hydrogen;
R⁴ is hydrogen;
Ar¹ is indazolyl, substituted with one methyl substituent;
Ar² is phenyl; and
X is O;
or a pharmaceutically acceptable salt thereof.

9. A pharmaceutical composition comprising a compound of claim 1, or a pharmaceutically acceptable salt thereof, and a pharmaceutically acceptable carrier.

* * * * *